United States Patent
Wang et al.

(10) Patent No.: US 11,318,005 B2
(45) Date of Patent: *May 3, 2022

(54) AQUEOUS ORAL CARE SOLUTIONS, METHODS, KITS, AND TOOTH SURFACES HAVING A COATING DERIVED FROM THE ORAL CARE SOLUTION

(71) Applicant: 3M INNOVATIVE PROPERTIES COMPANY, St. Paul, MN (US)

(72) Inventors: Yizhong Wang, Woodbury, MN (US); Jie J. Liu, Cottage Grove, MN (US); Richard P. Rusin, Woodbury, MN (US); Melinda B. Gustafson, Lake Elmo, MN (US); Ingo Haeberlein, Weilheim (DE); Carola A. Carrera Vidal, Plymouth, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/270,879

(22) PCT Filed: Aug. 27, 2019

(86) PCT No.: PCT/IB2019/057203
§ 371 (c)(1),
(2) Date: Feb. 24, 2021

(87) PCT Pub. No.: WO2020/044230
PCT Pub. Date: Mar. 5, 2020

(65) Prior Publication Data
US 2021/0177563 A1   Jun. 17, 2021

Related U.S. Application Data

(60) Provisional application No. 62/723,699, filed on Aug. 28, 2018.

(51) Int. Cl.
| | | |
|---|---|---|
| *A61C 19/06* | (2006.01) | |
| *A61C 19/08* | (2006.01) | |
| *A61K 8/19* | (2006.01) | |
| *A61K 8/21* | (2006.01) | |
| *A61K 8/23* | (2006.01) | |
| *A61Q 11/00* | (2006.01) | |

(52) U.S. Cl.
CPC ............ *A61C 19/063* (2013.01); *A61C 19/08* (2013.01); *A61K 8/19* (2013.01); *A61K 8/21* (2013.01); *A61K 8/23* (2013.01); *A61Q 11/00* (2013.01); *A61K 2800/48* (2013.01); *A61K 2800/592* (2013.01)

(58) Field of Classification Search
CPC ... A61K 5/02; A61K 6/00; A61K 6/02; A61Q 11/00
USPC ................................................. 424/129, 210
IPC ..................................................... A61Q 11/00
See application file for complete search history.

(56) References Cited

U.S. PATENT DOCUMENTS

| | | |
|---|---|---|
| 2,981,640 A | 4/1961 | Hill |
| 3,567,823 A | 3/1971 | Yamaga et al. |
| 4,012,839 A | 3/1977 | Hill |
| 6,461,161 B1 | 10/2002 | Ngo et al. |
| 6,923,990 B2 | 8/2005 | Capelli |
| 7,465,693 B2 | 12/2008 | Greer et al. |
| 8,968,709 B2 | 3/2015 | Yang et al. |
| 2002/0156130 A1 | 10/2002 | Melman |
| 2010/0247456 A1 | 9/2010 | Niederman et al. |

FOREIGN PATENT DOCUMENTS

| | | |
|---|---|---|
| JP | 2003171914 | 6/2003 |
| JP | 4229431 B2 | 2/2009 |
| WO | WO 2018/092889 A1 | 5/2019 |

OTHER PUBLICATIONS

DentistryIQ Editors, "SDI Introduces Riva Star Silver Diamine Fluoride Desensitizer," Apr. 23, 2018, [online]: *DentistryIQ*, [retrieved on Jan. 25, 2021], Retrieved from the internet: <https://www.dentistryiq.com/print/content/16367834>.

Garg et al., "Potassium Iodide Reversal of Silver Diamine Fluoride Staining: A Case Report," May/Jun. 2019, *Operative Dentistry*, 44(3):221-26.

Hamama et al., "Effect of silver diamine fluoride and potassium iodide on residual bacteria in dentinal tubules," 2015, *Australian Dental Journal*, 60:80-87.

Koizumi et al., "Effect of a silver diamine fluoride and potassium iodide-based desensitizing and cavity cleaning agent on bond strength to dentine," Feb. 19, 2016, *International Journal of Adhesion & Adhesives*, 68: 54-61.

"New USA SDF Market Entry," Aug. 1, 2018, *The Silver Bulletin*, [online]: Elevate Oral Care, [retrieved on Jan. 25, 2021], Retrieved from the internet: <http://www.elevateoralcare.com/silverbulletinv4>.

Nguyen et al., "Potassium Iodide. The Solution to Silver Diamine Fluoride Discoloration," Jun. 2017, *Advances in Dentistry and Oral Health*, 5(1):001-006.

(Continued)

*Primary Examiner* — Walter E Webb (74) *Attorney, Agent, or Firm* — 3M Innovative Properties Company (57) ABSTRACT

An aqueous oral care solution, a kit that includes such solution, a method of making such solution, a method of using such solution (e.g., a method of providing fluoride to a patient's tooth surface), and a tooth surface having a coating derived from the aqueous oral care solution, wherein the oral care solution includes: silver cations; thiocyanate anions provided by a thiocyanate source comprising Ca(SCN)2; fluoride anions; and water; wherein the molar ratio of silver to thiocyanate ions is up to 0.40:1, and water is up to 57 wt-%, based on the total weight of the solution.

19 Claims, 2 Drawing Sheets

(56) References Cited

OTHER PUBLICATIONS

Zhao et al. "Effect of Silver Diamine Fluoride and Potassium Iodide Treatment on Secondary Caries Prevention and Tooth Discolouration in Cervical Glass Ionomer Cement Restoration," Feb. 6, 2017, *International Journal of Molecular Sciences*, 18(340):1-12.
International Search Report and Written Opinion for PCT/IB2019/056376, dated Nov. 27, 2019, 12 pages.
International Search Report and Written Opinion for PCT/IB2019/057203, dated Jan. 29, 2020, 16 pages.

Fig. 3 ably to the extent that these terms are used in this specification. Terminology used in this description is for describing particular embodiments only and is not intended to be limiting.

AQUEOUS ORAL CARE SOLUTIONS, METHODS, KITS, AND TOOTH SURFACES HAVING A COATING DERIVED FROM THE ORAL CARE SOLUTION

CROSS REFERENCE TO RELATED APPLICATIONS

This application is a national stage filing under 35 U.S.C. 371 of PCT/IB2019/057203, filed 27 Aug. 2019, which claims the benefit of U.S. Provisional Application No. 62/723,699, filed 28 Aug. 2018, the disclosures of which are incorporated by reference in their entireties herein.

BACKGROUND

Fluoride treatment involves the application of fluoride to a tooth surface with the formation of fluorapatite and calcium fluoride.

There are two major in-office fluoride treatment methods currently in use. One treatment method uses a fluoride gel/foam in a tray. This method requires several grams of fluoride gel stored in a tray that is then placed into a patient's mouth onto the teeth. This tray is left in the mouth with the gel/foam in contact with the teeth for 1 to 4 minutes. The gel/foam formulation is an aqueous system that includes 2% sodium fluoride. This material requires the use of suction to pull the extra gel out of the mouth to avoid unnecessary high amounts of fluoride ingestion.

Another treatment method is a dental fluoride varnish. Most fluoride varnishes on the market are rosin/ethanol based formulations with a hydrophobic nature. The varnish is painted on the teeth and remains in place for several hours to allow for the fluoride to be released from the composition. Typically, dentists use fluoride varnishes for in-office fluoride treatments. Most dental fluoride varnishes include 5% sodium fluoride. The dose of varnish is about 0.5 gram. Dental varnishes place much smaller amounts of fluoride into a patient's mouth compared to fluoride gels/foams. Thus, fluoride ingestion is less with fluoride varnishes. Also, fluoride varnishes are easier to apply as they are simply painted on a patient's teeth; however, fluoride varnish treatments are more labor intensive than gel treatments, and fluoride varnish treatments leave the patient with an unpleasant "dirty teeth" feeling.

Compositions that are as simple to apply to teeth as varnishes and work in time periods as short as gel/foam formulations are desired.

SUMMARY OF THE DISCLOSURE

The present disclosure provides aqueous oral care solutions, methods of making such solutions, methods of treating (e.g., methods of providing fluoride to a patient's tooth surface) using such solutions, kits, and a treated tooth.

Such solutions can be used as in-office oral care solutions (e.g., as fluoride treatment solutions). They can be formulated into a solution that can be painted on a tooth surface if desired. They can provide similar fluoride efficacy to that of varnishes in the shorter periods of time of gel/foam formulations.

In one embodiment, the present disclosure provides an aqueous oral care solution that includes: silver cations; thiocyanate anions provided by a thiocyanate source including $Ca(SCN)_2$; fluoride anions; and water in an amount of up to 57 wt-%, based on the total weight of the solution; wherein the molar ratio of silver to thiocyanate ions is up to 0.40:1.

In certain embodiments of such solutions, an aqueous oral care solution includes: 12.5-20.2 wt-% silver cations; and 1.0-6.0 wt-% (preferably 2.2-3.5 wt-%) fluoride anions; wherein the weight percentages are based on the total weight of the solution; wherein the molar ratio of silver to thiocyanate ions is at least 0.10:1 and up to 0.40:1; and wherein the oral care solution forms a precipitate (e.g., silver-rich and $CaF_2$-rich layer) upon contact with additional water or saliva.

In another embodiment, the present disclosure provides a method of providing fluoride to a patient's tooth surface. The method involves applying an aqueous oral care solution as disclosed herein to the patient's tooth surface.

In another embodiment, the present disclosure provides a method of reducing the incidence of dental caries in a patient in need thereof. The method involves applying an aqueous oral care solution as disclosed herein to the patient's tooth surface.

In another embodiment, the present disclosure provides a method of reducing dentin sensitivity and/or root sensitivity (e.g., during cavity treatment and/or on an exposed root) in a patient in need thereof. The method includes applying an aqueous oral care solution as disclosed herein to the patient's tooth surface.

In another embodiment, the present disclosure provides a kit that includes an aqueous oral care solution as described herein and an applicator.

In another embodiment, the present disclosure provides a tooth including a tooth surface having dentin tubules and a coating disposed on the tooth surface, wherein the coating includes silver-rich particles and $CaF_2$-rich layer occluding at least a portion of the dentin tubules.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the phrases "at least one" and "one or more." The phrases "at least one of" and "comprises at least one of" followed by a list refers to any one of the items in the list and any combination of two or more items in the list.

The term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DETAILED DESCRIPTION OF ILLUSTRATIVE EMBODIMENTS

The present disclosure provides aqueous oral care solutions. The present disclosure also provides methods of providing fluoride to a patient's tooth surface, methods of reducing the incidence of dental caries, and methods of reducing dentin sensitivity and/or root sensitivity (e.g., during cavity treatment and/or on an exposed root) in a patient in need thereof. Such methods involve applying an aqueous oral care solution (e.g., a fluoride treatment solution) as described herein to the patient's tooth surface.

In certain embodiments, applying an aqueous oral care solution includes painting the oral care solution on the patient's tooth surface.

In certain embodiments, applying an aqueous oral care solution includes dispensing the oral care solution into a dental tray and attaching the tray having the oral care solution therein to the patient's tooth surface. In certain embodiments, the dental tray includes an orthodontic aligner treatment tray.

In certain embodiments, an aqueous oral care solution includes: silver cations; thiocyanate anions provided by a thiocyanate source comprising $Ca(SCN)_2$; fluoride anions; and water.

In certain embodiments, the silver ions (also referred to herein as silver cations) are present in an amount of at least 12.5 percent by weight (wt-%), at least 13.0 wt-%, at least 14.0 wt-%, or at least 15.0 wt-%, wherein the weight percentages are based on the total weight of the solution. In certain embodiments, the silver cations are present in an amount of up to 20.2 wt-%, up to 20.0 wt-%, up to 19.0 wt-%, or up to 18.0 wt-%, wherein the weight percentages are based on the total weight of the solution.

In certain embodiments, the source of silver cations is selected from silver fluoride, silver chloride, silver nitrate, silver diamine fluoride, and combinations thereof.

In certain embodiments, the fluoride ions (also referred to herein as fluoride anions) are present in an amount of at least 1.0 wt-%, at least 1.5 wt-%, at least 2.0 wt-%, or at least 2.2 wt-%, wherein the weight percentages are based on the total weight of the solution. In certain embodiments, the fluoride anions are present in an amount of up to 6.0 wt-%, up to 5.0 wt-%, up to 4.5 wt-%, up to 4.0 wt-%, up to 3.5 wt-%, wherein the weight percentages are based on the total weight of the solution.

In certain embodiments, the source of fluoride anions is selected from silver fluoride, silver diamine fluoride, sodium fluoride, ammonium fluoride, potassium fluoride, amine fluoride, and combinations thereof.

In certain embodiments, an aqueous oral care solution includes: 12.5-20.2 wt-% silver cations; and 2.2-3.5 wt-% fluoride anions; wherein the weight percentages are based on the total weight of the solution. In certain embodiments, thiocyanate ions are provided by $Ca(SCN)_2$, which is provided in an amount of 1 wt-% to 55 wt-%.

The molar ratio of silver to thiocyanate ions is up to 0.40:1, up to 0.39:1, or up to 0.38:1. In certain embodiments, the molar ratio of silver to thiocyanate ions is at least 0.10:1, at least 0.15:1, at least 0.20:1, at least 0.25:1, at least 0.27:1, or at least 0.30:1. In certain embodiments, the source of thiocyanate ions (also referred to herein as thiocyanate anions) includes $Ca(SCN)_2$ and optionally a secondary source of thiocyanate ions selected from ammonium thiocyanate, sodium thiocyanate, potassium thiocyanate, guanidinium thiocyanate, and combinations thereof.

In certain embodiments, an aqueous oral care solution includes water in an amount of at least 20 wt-%, at least 25 wt-%, or at least 30 wt-%, based on the total weight of the solution. The amount of water is up to 57 wt-%, up to 55 wt-%, or up to 50 wt-%, based on the total weight of the solution.

Upon contact with additional water or saliva in the oral environment, the oral care solution forms a precipitate (i.e., a solid formed from the solution). The precipitate includes Ag, AgSCN, and $CaF_2$. The resultant silver-containing precipitate is believed to provide antibacterial effect. While not being bound by theory, it is believed that the $CaF_2$, AgSCN, fluoride ions, and/or excess thiocyanate ions, complex with calcium in the tooth.

In certain embodiments, an oral care solution includes: 12.5-20.2 wt-% silver cations; and 1.0-6.0 wt-% (or 2.2-3.5 wt-%) fluoride anions; wherein the weight percentages are based on the total weight of the solution; and thiocyanate anions, wherein a molar ratio of silver to thiocyanate ions is at least 0.10:1 and up to 0.40:1; wherein the oral care solution forms a precipitate upon contact with additional water or saliva.

Oral care solutions of the present disclosure are aqueous solutions, although they may include a small amount of one or more organic solvents. Examples of organic solvents are selected from ethanol, isopropanol, dimethyl sulfoxide (DMSO), isoprene sulfone (IS), butadiene sulfone (BS), piperylene sulfone (PS), ethyl acetate, methyl acetate, isopropyl acetate, acetone, methyl ethyl ketone (MEK), methyl isobutyl ketone (MIBK), and combinations thereof.

Preferably, the aqueous oral care solutions are free of organic solvents that function as liquid carriers (as opposed to organic solvents that are used as carriers/solvents for flavorants or sweeteners). For example, certain additives may be provided as a solution or dispersion in an organic solvent as a liquid carrier. If there is any organic solvent (that functions as a liquid carrier) present in aqueous oral care solutions of the present disclosure, it is present in an amount of less than 5 wt-%, based on the total weight of the aqueous solution.

Preferably, aqueous oral care solutions of the present disclosure do not stain teeth. This can be determined by combining an oral care solution in a ratio of 3:1 with a 1% phosphate solution and exposing the mixture to a blue LED light with wavelength of 430-480 nm and output of approximately 1500 mW/cm$^2$ (−10%/+20%), such as that commercially available under the Tradename 3M ELIPAR DEEP-CURE-S LED curing light (available from 3M Company, St. Paul, Minn.), for 20 seconds, to see whether the mixture forms a black precipitate. If no black precipitate forms, the solution will not stain teeth.

Aqueous oral care solutions of the present disclosure are not generally shelf stable in that they form a layered composition; however, shaking or stirring the composition may result in a homogeneous composition.

Additional Optional Active Agents

Aqueous oral care solutions of the present disclosure can also contain one or more active agents in addition to a source of fluoride. When included, the one or more additional active agents usually, but not always, include one or more active agents that are active in the oral cavity against disorders, diseases, or conditions of the teeth, gums, cheeks, tongue, roof of the mouth, and the like.

Examples of additional active agents that can be employed include one or more other fluorine-containing compounds, such as sodium monofluorophosphate, stannous fluoride, calcium fluoride, strontium fluoride, zinc fluoride, zinc potassium fluoride, potassium magnesium fluoride, and combinations thereof.

Examples of additional active agents that can be employed include one or more whitening agents, anticalculus agents, remineralization agents, stannous sources, antimicrobial agents, antioxidants, saliva stimulating agents, breath freshening agents, antiplaque agents, anti-inflammatory agents, $H_2$ antagonists, desensitizing agents, nutrients, and proteins. Various combinations of such additional active agents may be used if desired. When employed, one or more additional active agents will be typically used in amounts sufficient to achieve their intended effect.

When employed, the whitening agents can be a wide variety of suitable whitening agents. The whitening agents can include, for example, a peroxide whitening agent, a non-peroxide whitening agent, or both. Peroxide whitening agents include hydrogen peroxide, peroxide of alkali or alkaline earth metals, such as sodium peroxide, potassium peroxide, lithium peroxide, magnesium peroxide, calcium peroxide, barium peroxide, and the like, glyceryl hydrogen peroxide, alkyl hydrogen peroxide, dialkyl peroxide, peroxy acids or peroxy acid salts, benxoyl peroxide, urea peroxide, and the like. Hydrogen peroxide is most common. Non-peroxide whitening agents include chlorine dioxide, chlorites, and hypochlorites. Chlorites and hyperchlorites are typically in the form of alkali or alkaline earth metal salts, such as salts of lithium, potassium, sodium, magnesium, calcium, or barium. Colorants, titanium dioxide, and hydroxyapatite can also be used.

When employed, the anticalculus agents can be a wide variety of suitable anticalculus agents. The anticalculus agents can include, for example, phosphates, polyphosphates, such as pyrophosphates, polyolefin sulfonates, polyolefin phosphates, diphosphonates, phosphonoalkane carboxylic acids, and salts thereof, typically alkali metal or ammonium salts.

When employed, the remineralization agents can be a wide variety of suitable remineralization agents. The remineralization agents can include, for example, materials that release calcium ions, phosphorous-containing ions, or both, such as calcium phosphate (e.g., mono-, di-, and/or tricalcium phosphate), hydroxyapatite, calcium carbonate, and the like.

Examples of materials that release calcium ions are calcium salts that are water soluble, such as those selected from calcium chloride, calcium nitrate, calcium gluconate, calcium lactate gluconate, calcium acetate, hydrates thereof, and combinations thereof. In certain embodiments, the calcium salt is selected from calcium chloride, calcium nitrate, hydrates thereof, and combinations thereof.

A calcium salt can also be used to modulate the fluoride release profile.

When employed, the stannous sources can be a wide variety of suitable sources of stannous ions. The stannous ion sources can include, for example, stannous halides, organic stannous carboxylate salts, such as stannous formate, stannous acetate, stannous gluconate, stannous lactate, stannous tartrate, and stannous citrate. When the fluoride source is stannous fluoride, it can also function as a stannous source.

When employed, the antimicrobial agents can include a wide variety of orally acceptable antimicrobial agents. Examples include triclosan, 8-hydroxyquinoline, zinc ion, stannous ion, cupric compounds, phthalic acid and salts thereof, quaternary ammonium compounds, sanguinarine, salicylanilide, salicylic acid, thymol, eugenol, neomycin, kanamycin, clindamycin, amoxicillin, tetracycline, doxycycline, minocycline, metronidazole, chlorohexidine, and the like.

When employed, the antioxidants can be a wide variety of orally acceptable antioxidants. Examples include butylated hydroxy anisone, butylated hydroxy toluene, vitamin A, carotenoids, vitamin E, flavonoids, polyphenols, ascorbic acid or salts thereof, chlorophyll, melatonin, and the like.

When employed, the saliva stimulants can be a wide variety of orally acceptable saliva stimulants. Examples include citric acid, lactic acid, succinic acid, ascorbic acid, adipic acid, fumaric acid, and tartaric acid.

When employed, the breath freshening agents can be a wide variety of orally acceptable breath freshening agents. Examples include zinc salts such as zinc salts of gluconate, citrate, chlorite, alpha-ionone, and the like.

When employed, the antiplaque agents can be a wide variety of orally acceptable antiplaque agents. Examples include stannous salts, salts of copper, magnesium or strontium, dimethicone copolyols, such as cetyl dimethicone copolyol, papain, glucamylase, glucose oxidase, urea, calcium lactate, calcium glycerophosphate, strontium polyacrylates, and the like. Further examples of antiplaque agents include biofilm inhibition agents, particularly those described in U.S. Pat. No. 8,968,709 (Yang et al.).

When employed, the anti-inflammatory agents can be a wide variety of orally acceptable anti-inflammatory agents. Examples include steroids such as flucinolone and hydrocortisone, non-steroidal anti-inflammatory drugs such as ketorolac, flurbiprofen, ibuprofen, naproxen, indomethacin, diclofenac, etodolac, indomethacin, sulindac, tolmetin, ketoprofen, fenoprofen, piroxicam, nabumetone, acetyl salicylic acid, salicylic acid, diflunisal, meclofenamate, mefenamic aicd, oxyphenbutazone, phenylbutazone, and the like.

When employed, the $H_2$ antagonists can be a wide variety of orally acceptable $H_2$ antagonists. Examples include cimetidine, etinidine, ranitidine, tiotidine, lupitidine, denetidine, famotidine, roxatidine, pifatidine, lamtidine, zaltidine, nizatidine, mifentidine, ramixotidine, loxtidine, bisfentidine, sufotidine, ebrotidine, impromdine, and the like.

When employed, the desensitizing agents can be a wide variety of orally acceptable desensitizing agents. Examples include potassium citrate, potassium chloride, potassium tartrate, potassium bicarbonate, potassium oxalate, potassium nitrate, strontium salts, arginine, acetyl salicylic acid or salts thereof, salicylic acid or salts thereof, codeine, acetaminophen, and the like.

When employed, the nutrients can be a wide variety of orally acceptable nutrients. Examples include vitamins, such as vitamins C, D, thiamine, riboflavin, folic acid, nicotinamide, niacin, pyridoxine, bioflavonoids, and the like, supplements, such as amino acids, lipotropics, fish oil, polyunsaturated fatty acids, eicosapentanoic acid, docosahexanic acid, coenzyme Q10, ubiquinone, minerals such as potassium, and the like.

When employed, the proteins can include a wide variety of orally acceptable proteins. Examples include milk proteins, peroxide producing enzymes, amylase, papain, glucoamylase, glucose oxidase, and the like.

Buffers

Aqueous oral care solutions of the present disclosure can include a pharmaceutically acceptable buffer. The type and amount of such buffer is selected to provide an oral care solution with a pH of at least 5.5, at least 6, or at least 6.5. In certain embodiments, the type and amount of such buffer is selected to provide an oral care solution with a pH of up to 9, up to 8.5, up to 7.5, or up to 7. In certain embodiments, the type and amount of such buffer is selected to provide an oral care solution with a pH of 6.5 to 7.5, or a pH of 7.0. A wide variety of suitable pharmaceutically acceptable buffers can be included. Examples include acetate (e.g., sodium acetate), sodium carbonate, citrate (e.g., sodium citrate), tartrate, glycylglycine, histidine, glycine, lysine, arginine, sodium dihydrogen phosphate, disodium hydrogen phosphate, sodium phosphate, tris(hydroxymethyl)-aminomethane, or mixtures thereof.

Thickeners

In certain embodiments, aqueous oral care solutions of the present disclosure include a thickener to provide a solution with a suitable viscosity to allow for the desired method of application. For example, a suitable thickener in a sufficient amount may be used to achieve a solution viscosity adequate to maintain the solution in an inverted mouthpiece tray applicator for up to four minutes (typical time for a professionally applied fluoride treatment), and yet be fluid enough to have acceptable handling characteristics for the dental operator (e.g., when dispensing into a dental tray applicator). Or, a suitable thickener in a sufficient amount may be used to achieve a solution viscosity adequate to paint on a tooth surface.

In certain embodiments, the type and amount of thickener is selected to provide an oral care solution with a viscosity of at least 0.5 Pascal seconds at a shear rate of 1.0/second. In certain embodiments, a type and amount of thickener is selected to provide an oral care solution with a viscosity of up to 500 Pascal seconds at a shear rate of 1.0/second.

In certain embodiments, a thickener is present in an oral care solution in an amount of less than 2.5 wt-%, based on the total weight of the aqueous solution. In certain embodiments, a thickener is present in an amount of at least 0.5 wt-%, based on the total weight of the aqueous solution.

Suitable thickeners are typically those that are generally safe for human ingestion (FDA approved for internal use), do not bind fluoride ions, and do not significantly affect the bioavailability of fluoride ions.

In certain embodiments, the thickener is selected from natural gums, non-acid cellulose derivatives (e.g., hydroxyethyl cellulose), inorganic fillers (e.g., colloidal silica, fumed silica, alumina, titania, and zinc oxide), alkylene oxide polymers (e.g., polyethylene glycol, polypropylene glycol, and copolymers of polyethylene glycol and polypropylene glycol), non-acid modified starches, and combinations thereof.

Optional Additives

In certain embodiments, aqueous oral care solutions of the present disclosure include one or more optional additives including flavoring agents (i.e., flavorants) and sweeteners. Other optional additives include surfactants. Various combinations of such additives may be used if desired.

In certain embodiments, aqueous oral care solutions of the present disclosure include a sweetener. A wide variety of orally acceptable sweeteners can be used. Common sweeteners include xylitol, sorbitol, sucralose, aspartame, saccharin, usually sodium saccharine, and the like. When present, a sweetener can be used in any suitable amount, most often in an amount sufficient to impart a pleasant sweetness to the solution. The suitable amount is typically 0.5 wt-% to 15 wt-%, based on the total weight of the aqueous solution.

In certain embodiments, aqueous oral care solutions of the present disclosure include a flavoring agent. A wide variety of orally acceptable flavoring agents can be used. Common flavoring agents include peppermint oil, spearmint oil, cherry flavor, citric acid, orange flavor, vanilla, strawberry flavor, coconut flavor, and bubble gum flavor. When present, a flavoring agent can be used in any suitable amount, most often in an amount sufficient to impart a desired flavor to the solution. The suitable amount is typically 1 wt-% to 4 wt-%, based on the total weight of the aqueous solution.

In certain embodiments, aqueous oral care solutions of the present disclosure include a surfactant. Typically, such surfactant is an anionic surfactant, examples of which include polysorbate, glycerol, polyglycerol-based surfactant, or combinations thereof. When present, a surfactant can be used in any suitable amount, most often in an amount sufficient to impart wetability. A suitable amount is typically 0.1 wt-% to 5.0 wt-%, based on the total weight of the aqueous solution.

Kits

In certain embodiments, aqueous oral care solutions of the present disclosure are included in kits. Typically, such kit includes an applicator (e.g., dental brush, cotton tip swab) for the oral care solution. Such applicator may be integrated into a container having the oral care solution therein.

In certain embodiments, the oral care solution is provided in individual sealed unit dose containers. In use, the seals of such individual sealed unit dose containers are broken and the solution picked up with the applicator and the solution applied to a tooth surface.

In certain embodiments, the oral care solution is provided in a multi-dose container. In use, a drop of the solution can be dispensed onto a tray, piece of plastic, piece of paper, dish, well, pan, etc., and the solution picked up with the applicator and the solution applied to a tooth surface.

In certain embodiments, the kit may further include one or more of a dental restorative, a tray, a dish, a well, or a pan. Examples of dental restorative include, but are not limited to, an adhesive, primer, cement, liner, sealant, amalgam, resin, resin composite, glass ionomer, resin-modified glass ionomer, glass-ceramic, ceramic, metal, plastic, or combination thereof.

Methods of Making and Using

An aqueous oral care solution of the present disclosure can be made using any techniques known to one of skill in the art. In certain embodiments, the components are added together into water and dissolved, in no particular order. Alternatively, the order of addition can be important in obtaining a solution. For example, in certain embodiments, the source(s) of silver and fluoride (e.g., AgF) are dissolved in water first and then the source of thiocyanate (comprising $Ca(SCN)_2$ and optionally one or more secondary sources of thiocyanate) is added. Alternatively, each component can be dissolved in water separately and then combined to form an aqueous oral care solution.

In certain embodiments, an aqueous oral care solution of the present disclosure is used in a method of providing fluoride to a patient's tooth surface. The method includes applying the aqueous oral care solution described herein to the patient's tooth surface.

In certain embodiments, an aqueous oral care solution of the present disclosure is used in a method of reducing the incidence of dental caries (e.g., by preventing or arresting dental caries) in a patient in need thereof. The method includes applying the aqueous oral care solution described herein to the patient's tooth surface.

In certain embodiments, an aqueous oral care solution of the present disclosure is used in a method of reducing dentin sensitivity and/or root sensitivity (e.g., during cavity treatment and/or on an exposed root) in a patient in need thereof. The method includes applying the aqueous oral care solution described herein to the patient's tooth surface.

In certain embodiments, a patient's tooth surface that is treated with a method as described herein includes enamel, dentin, cementum, root, or combinations thereof.

In certain embodiments of the methods described above, applying includes painting the oral care solution on the patient's tooth surface. In certain embodiments of the methods described above, applying includes dispensing the oral care solution into a dental tray (e.g., an orthodontic aligner treatment tray) and attaching the tray having the oral care solution therein to the patient's tooth surface.

In certain embodiments of the methods described above, the oral care solution is subsequently dried (e.g., using flowing air) after being applied to the tooth surface. The source of flowing air can be delivered from an air compressor that delivers at high pressure limits of 115 pounds per square inch (psi). One example of a suitable air compressor is an Osprey Compressor from RAMVAC (models OSP22, OSP13, OSP23, OSP24, OSP25, OSP28) commercially available from Dental EZ Integrated Solutions of Malvern, Pa., or Patterson Dental of St. Paul, Minn. Another example of an air compressor is AirStar Neo air compressors by AIR TECHNIQUES (Models such as AirStar 10 Neo, AirStar 21 Neo) commercially available from Patterson Dental of St. Paul, Minn. Alternatively, the pressurized gas device could be a typical air/water syringe found in most dental offices for delivering pressurized air. Optimum air pressure with a typical dental air/water syringe is 40-80 psi. Such syringes are used to dry the teeth or to blow scaled calculus off the teeth. One example of such a syringe is a Johnson-Promident 3-Way Air/Water Syringe commercially available from Patterson Dental Supply Inc., Patterson Item #: 404-1893. Regardless, the gas is blown by some pressurized gas source, and could be air or some other inert gas or gas mixture. For example, the gas could be nitrogen, helium, argon, carbon dioxide, or nitrous oxide. The source of pressurized gas could be part of a permanently installed "in-house" pressurized air/gas system or a hand held, self-contained canister.

In certain embodiments of the methods described above, water is subsequently applied to the oral care solution after the oral care solution is applied to the tooth surface to form a precipitate thereon (i.e., on the tooth surface). In certain embodiments of the methods described above, saliva is subsequently allowed to contact the oral care solution on the tooth surface to form a precipitate thereon (i.e., on the tooth surface).

In certain embodiments of the methods described above, the methods further include placing a dental restorative on the tooth surface having the oral care solution applied thereto (either before or after the solution is dried or a precipitate is formed on the tooth surface). Examples of dental restorative include, but are not limited to, an adhesive, primer, cement, liner, sealant, amalgam, resin, resin composite, glass ionomer, resin-modified glass ionomer, glass-ceramic, ceramic, metal, plastic, or combination thereof.

In certain embodiments, a tooth is provided that includes a tooth surface having dentin tubules and a coating disposed on the tooth surface, wherein the coating comprises silver-rich particles and $CaF_2$-rich layer occluding at least a portion of the dentin tubules.

Figure 2:
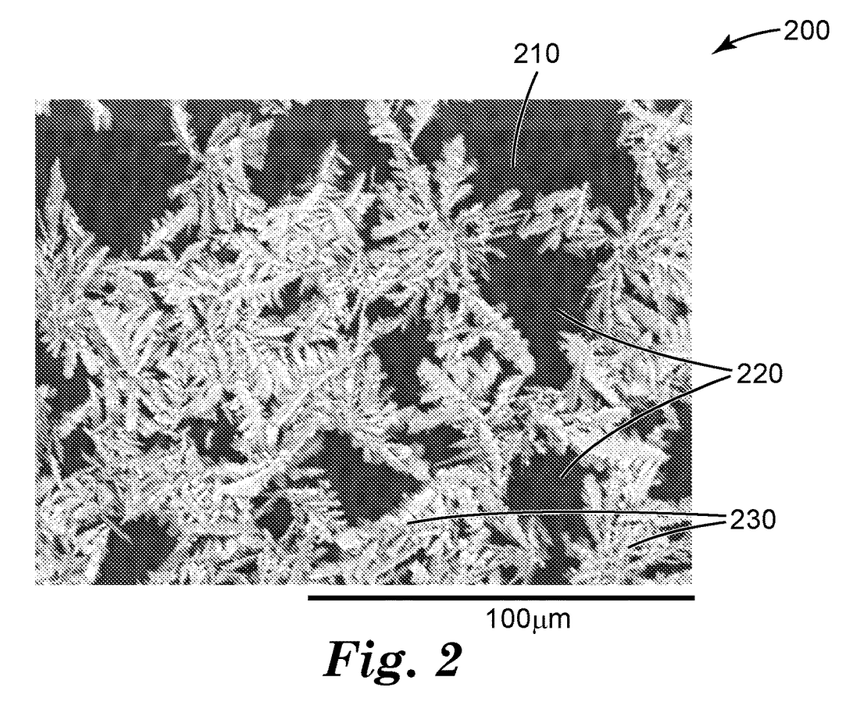
FIG. 2 is an SEM of the material of Comparative Example CE-17, which is a dentin surface that was treated with Comparative Example CE-10 solution.
Figure 3:
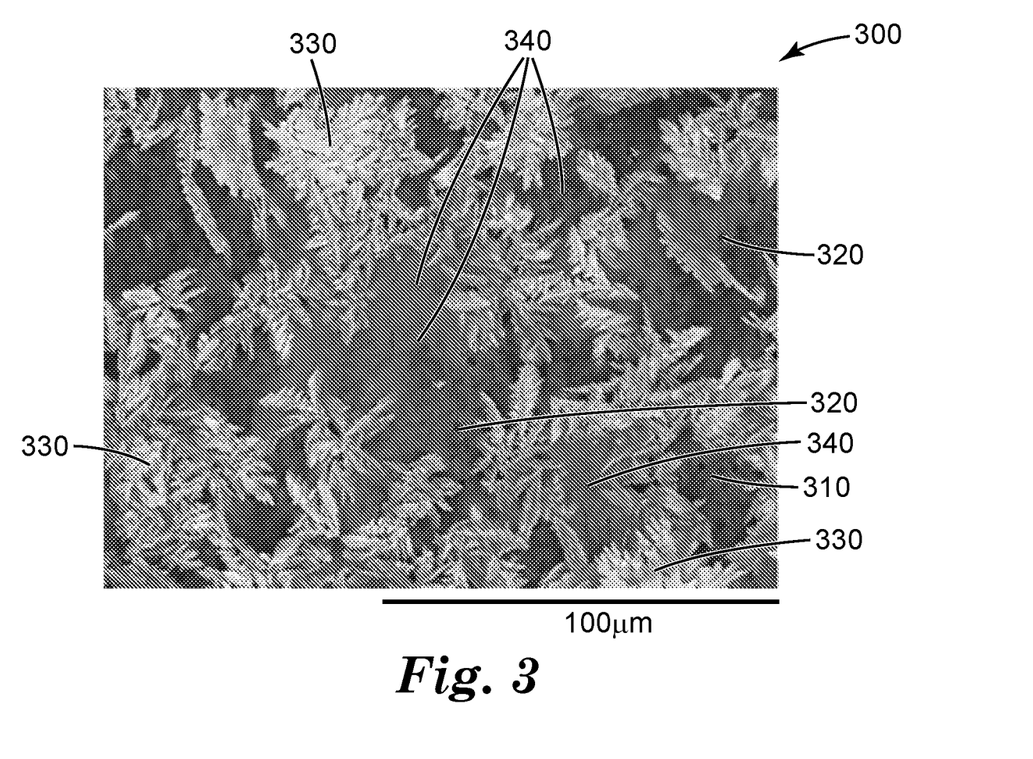
FIG. 3 is an SEM of the material of Example Ex-27, which is a dentin surface that was treated with Example Ex-7 solution.

As shown in the SEM of FIG. 3, a dentin surface treated with an aqueous oral care solution of the present disclosure (Example Ex-7 solution), which contains $Ca(SCN)_2$ tetrahydrate, a tooth surface 300 has a dentin surface 310 with dentin tubule openings 320 and silver-rich particles 330 (e.g., in the form of "snow flake-like" silver crystals) and a calcium fluoride-rich layer 340 dried on the dentin surface, thereby occluding at least a portion of the dentin tubules. This is in contrast to the SEM of FIG. 1, which shows a tooth surface 100 with a dentin surface 110 having numerous (non-occluded) dentin tubule openings 120, and the SEM of FIG. 2, which shows a tooth surface 200 with a dentin surface 210 having (non-occluded) dentin tubule openings 220 and silver-rich particles 230 (e.g., in the form of "snow flake-like" silver crystals) but no calcium fluoride-rich layer.

Occluded dentin tubules contribute to the reduction of the incidence of dental caries (e.g., by preventing or arresting dental caries), the reduction of dentin sensitivity and/or root sensitivity (e.g., during cavity treatment and/or on an exposed root), and/or the remineralization and strengthening of the tooth structure.

Exemplary Embodiments

Embodiment 1 is an aqueous oral care fluoride solution comprising: silver cations; thiocyanate anions provided by a thiocyanate source comprising calcium thiocyanate (Ca(SCN)$_2$); fluoride anions; and water in an amount of up to 57 wt-% (up to 55 wt-%, or up to 50 wt-%), based on the total weight of the solution; wherein the molar ratio of silver to thiocyanate ions is up to 0.40:1.

Embodiment 2 is the oral care solution of embodiment 1 comprising at least 12.5 wt-%, at least 13.0 wt-%, at least 14.0 wt-%, or at least 15.0 wt-%, silver cations, based on the total weight of the solution.

Embodiment 3 is the oral care solution of embodiment 1 or 2 comprising up to 20.2 wt-%, up to 20.0 wt-%, up to 19.0 wt-%, or up to 18.0 wt-%, silver cations, based on the total weight of the solution.

Embodiment 4 is the oral care solution of any of the preceding embodiments comprising at least 1.0 wt-%, at least 1.5 wt-%, at least 2.0 wt-%, or at least 2.2 wt-%, fluoride anions, based on the total weight of the solution.

Embodiment 5 is the oral care solution of any of the preceding embodiments comprising up to 6.0 wt-%, up to 5.0 wt-%, up to 4.5 wt-%, up to 4.0 wt-%, or up to 3.5 wt-%, fluoride anions, based on the total weight of the solution.

Embodiment 6 is the oral care solution of any of the preceding embodiments wherein the molar ratio of silver to thiocyanate ions is up to 0.39:1, or up to 0.38:1.

Embodiment 7 is the oral care solution of any of the preceding embodiments wherein the molar ratio of silver to thiocyanate ions is at least 0.10:1, at least 0.15:1, at least 0.20:1, at least 0.25:1, at least 0.27:1, or at least 0.30:1.

Embodiment 8 is the oral care solution of any of the preceding embodiments wherein calcium thiocyanate (Ca(SCN)$_2$) is provided in an amount of at least 1 wt-%, based on the total weight of the solution.

Embodiment 9 is the oral care solution of any of the preceding embodiments wherein calcium thiocyanate (Ca(SCN)$_2$) is provided in an amount of up to 55 wt-%, based on the total weight of the solution.

Embodiment 10 is the oral care solution of any of the preceding embodiments comprising at least 20 wt-%, at least 25 wt-%, or at least 30 wt-%, water, based on the total weight of the solution.

Embodiment 11 is the oral care solution of any of the preceding embodiments comprising: 12.5-20.2 wt-% silver cations; and 1.0-6.0 wt-% fluoride anions; wherein the weight percentages are based on the total weight of the solution; wherein the molar ratio of silver to thiocyanate ions is at least 0.10:1 and up to 0.40:1; and wherein the oral care solution forms a precipitate (e.g., Ag and CaF$_2$) upon contact with additional water or saliva.

Embodiment 12 is the oral care solution of any of the preceding embodiments comprising: 12.5-20.2 wt-% silver cations; 1-55 wt-% Ca(SCN)$_2$; and 2.2-3.5 wt-% fluoride anions, based on the total weight of the solution.

Embodiment 13 is the oral care solution of any of the preceding embodiments comprising a source of silver cations selected from silver fluoride, silver chloride, silver nitrate, silver diamine fluoride, and combinations thereof.

Embodiment 14 is the oral care solution of any of the preceding embodiments comprising a source of fluoride anions selected from silver fluoride, silver diamine fluoride, sodium fluoride, ammonium fluoride, potassium fluoride, amine fluoride, and combinations thereof.

Embodiment 15 is the oral care solution of any of the preceding embodiments comprising a secondary source of thiocyanate anions selected from ammonium thiocyanate, sodium thiocyanate, potassium thiocyanate, guanidinium thiocyanate, and combinations thereof.

Embodiment 16 is the oral care solution of any of the preceding embodiments further comprising a pharmaceutically acceptable buffer.

Embodiment 17 is the oral care solution of any of the preceding embodiments further comprising a thickener.

Embodiment 18 is the oral care solution of embodiment 17 wherein the thickener is present in an amount of 0.5-2.5 wt-%, based on the total weight of the solution.

Embodiment 19 is the oral care solution of any of the preceding embodiments which has a pH of 5.5 to 9.

Embodiment 20 is the oral care solution of any of the preceding embodiments comprising less than 5 wt-% organic solvent, based on the total weight of the solution.

Embodiment 21 is the oral care solution of embodiment 20 wherein the organic solvent is selected from ethanol, isopropanol, dimethyl sulfoxide (DMSO), isoprene sulfone (IS), butadiene sulfone (BS), piperylene sulfone (PS), ethyl acetate, methyl acetate, isopropyl acetate, acetone, methyl ethyl ketone (MEK), methyl isobutyl ketone (MIBK), and combinations thereof.

Embodiment 22 is the oral care solution of any of the preceding embodiments further comprising one or more active agents.

Embodiment 23 is the oral care solution of embodiment 22 wherein the one or more active agents comprise whitening agents, anticalculus agents, remineralization agents, stannous sources, antimicrobial agents, antioxidants, saliva stimulating agents, breath freshening agents, antiplaque agents, anti-inflammatory agents, H$_2$ antagonists, desensitizing agents, nutrients, proteins, or combinations thereof.

Embodiment 24 us the oral care solution of any of the preceding embodiments further comprising a flavoring agent.

Embodiment 25 is the oral care solution of any of the preceding embodiments further comprising a sweetener.

Embodiment 26 is the oral care solution of any of the preceding embodiments further comprising calcium cations.

Embodiment 27 is the oral care solution of embodiment 26 comprising a secondary source of calcium cations selected from calcium chloride, calcium nitrate, calcium gluconate, calcium lactate gluconate, calcium acetate, hydrates thereof, and combinations thereof.

Embodiment 28 is the oral care solution of any of the preceding embodiments further comprising a surfactant.

Embodiment 29 is the oral care solution of embodiment 28 wherein the surfactant is an anionic surfactant.

Embodiment 30 is the oral care solution of embodiment 29 wherein the anionic surfactant is selected from polysorbate, glycerol, polyglycerol-based surfactant, and combinations thereof.

Embodiment 31 is the oral care solution of any of the preceding embodiments which does not stain teeth.

Embodiment 32 is the oral care solution of embodiment 31, which when combined 3:1 with a 1% phosphate solution and exposing the mixture to a blue LED light with wavelength of 430-480 nm and output of approximately 1500 mW/cm$^2$ for 20 seconds, does not form a black precipitate.

Embodiment 33 is a method of providing fluoride to a patient's tooth surface, the method comprising applying the aqueous oral care solution of any of the preceding embodiments to the patient's tooth surface.

Embodiment 34 is a method of reducing the incidence of dental caries (e.g., by preventing or arresting dental caries) in a patient in need thereof, the method comprising applying an aqueous oral care solution of any one of embodiments 1 to 32 to the patient's tooth surface.

Embodiment 35 is a method of reducing dentin sensitivity and/or root sensitivity (e.g., during cavity treatment and/or on an exposed root) in a patient in need thereof, the method comprising applying an aqueous oral care solution of any one of embodiments 1 to 32 to the patient's tooth surface.

Embodiment 36 is the method of any of embodiments 33 to 35 wherein the patient's tooth surface comprises enamel, dentin, cementum, root, or combinations thereof.

Embodiment 37 is the method of any of embodiments 33 to 36 wherein applying comprises painting the oral care solution on the patient's tooth surface.

Embodiment 38 is the method of any of embodiments 33 to 36 wherein applying comprises dispensing the oral care solution into a dental tray (e.g., an orthodontic aligner treatment tray) and attaching the tray having the oral care solution therein to the patient's tooth surface.

Embodiment 39 is the method of any of embodiments 33 to 38 wherein the oral care solution is subsequently dried (e.g., using flowing air) after being applied to the tooth surface.

Embodiment 40 is the method of any of embodiments 33 to 38 wherein water is subsequently applied to the oral care solution after the oral care solution is applied to the tooth surface to form a precipitate thereon (i.e., on the tooth surface).

Embodiment 41 is the method of any of embodiments 33 to 38 wherein saliva is subsequently allowed to contact the oral care solution on the tooth surface to form a precipitate thereon (i.e., on the tooth surface).

Embodiment 42 is the method of any of embodiments 33 to 41 further comprising placing a dental restorative on the tooth surface having the oral care solution applied thereto (either before or after the solution is dried or a precipitate is formed on the tooth surface).

Embodiment 43 is the method of embodiment 42 wherein the dental restorative comprises an adhesive, primer, cement, liner, sealant, amalgam, resin, resin composite, glass ionomer, resin-modified glass ionomer, glass-ceramic, ceramic, metal, plastic, or combination thereof.

Embodiment 44 is a kit comprising an aqueous oral care solution of any one of embodiments 1 to 32 and an applicator (e.g., dental brush, cotton tip swab).

Embodiment 45 is the kit of embodiment 44 wherein the oral care solution is provided in individual sealed unit dose containers.

Embodiment 46 is the kit of embodiment 44 wherein the oral care solution is provided in a multi-dose container.

Embodiment 47 is the kit of any of embodiments 44 to 46 wherein the applicator is integrated into the container having the oral care solution therein.

Embodiment 48 is the kit of any of embodiments 44 to 47 further comprising a dental restorative.

Embodiment 49 is the kit of embodiment 48 wherein the dental restorative comprises an adhesive, primer, cement, liner, sealant, amalgam, resin, resin composite, glass ionomer, resin-modified glass ionomer, glass-ceramic, ceramic, metal, plastic, or combination thereof.

Embodiment 50 is the kit of any of embodiments 44 to 49 further comprising a tray, a dish, a well, or a pan.

Embodiment 51 is a method of making an aqueous oral care solution of any one of embodiments 1 to 32 comprising combining a source of silver and a source of fluoride (which may be the same, e.g., AgF) in water and dissolving therein; and adding a source of thiocyanate comprising $Ca(SCN)_2$ and optionally one or more secondary sources of thiocyanate, and dissolving therein to form an aqueous oral care solution.

Embodiment 52 is a tooth comprising a tooth surface having dentin tubules and a coating disposed on the tooth surface, wherein the coating comprises silver-rich particles and $CaF_2$-rich layer occluding at least a portion of the dentin tubules.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims. Unless otherwise stated, all amounts are in weight percent.

TABLE 1

| Materials | | |
|---|---|---|
| Description | Source | Location |
| Ammonium chloride ($NH_4Cl$) | VWR | West Chester, PA |
| Ammonium iodide ($NH_4I$) | Honeywell Specialty Chemical | Seelze, Germany |
| Ammonium thiocyanate ($NH_4SCN$) | Alfa Aesar | Ward Hill, MA |
| Calcium thiocyanate tetrahydrate ($Ca(SCN)_2$ tetrahydrate) | Sigma Aldrich | St Louis, MO |
| Disodium hydrogen citrate sesquihydrate | Alfa Aesar | Ward Hill, MA |
| Sodium carbonate | EMD | Gibbstown, NJ |
| Potassium phosphate monobasic | Sigma Aldrich | St Louis, MO |
| Potassium sulfate | J. T. Baker | Phillipsburg, NJ |
| Silver fluoride (AgF) | Oakwood Chemical | West Columbia, SC |
| Silver diamine fluoride solution 38%, commercially available as ADVANTAGE ARREST silver diamine fluoride | Elevate Oral Care | West Palm Beach, FL |

Example Preparation and Assessment

For each Example or Comparative Example, 0.5 gram of silver fluoride was weighed in a plastic tube and 0.8 gram of deionized (DI) water was added and mixed well to form solution. To achieve the weight percentages reported in the Example tables below, the remaining components of each Example or Comparative Example were weighed out and combined in a weighing boat as a dry mixture. The additional dry components were then slowly added into silver fluoride solution while mixing. This was an exothermic process, as heat was generated during the addition of thiocyanate. Initially a paste-like precipitate formed as the additional dry components were partially added. This is reported in the tables below.

The slow addition of the remaining dry components continued. For the working Examples, the precipitate completely dissolved after the addition of an appropriate amount of thiocyanate. After the complete addition of all the remaining dry components, including calcium thiocyanate, the Example solutions became cloudy, were mixed on a vortex mixer and remained cloudy. The Example solutions were allowed to stand undisturbed for 1 week at room temperature. After 1 week the Example solutions were observed to have separated into two phases: a clear solution on top and a cloudy bottom layer.

For the Comparative Examples, the addition of the remaining dry components did not re-dissolve the initial precipitate, with the exception of Comparative Example CE-10.

TABLE 2

COMPARATIVE EXAMPLES CE-1 to CE-5.

| Components | CE-1 | CE-2 | CE-3 | CE-4 | CE-5 |
|---|---|---|---|---|---|
| AgF | 16.7 | 16.7 | 16.7 | 16.7 | 16.7 |
| Disodium hydrogen citrate sesquihydrate | 50.0 | 0.0 | 0.0 | 0.0 | 0.0 |
| Sodium carbonate | 0.0 | 50.0 | 0.0 | 0.0 | 0.0 |
| Potassium phosphate monobasic | 0.0 | 0.0 | 50.0 | 0.0 | 0.0 |
| $NH_4Cl$ | 0.0 | 0.0 | 0.0 | 50.0 | 0.0 |
| $Ca(SCN)_2$ tetrahydrate | 0.0 | 0.0 | 0.0 | 0.0 | 0.0 |
| Potassium sulfate | 0.0 | 0.0 | 0.0 | 0.0 | 50.0 |
| DI water | 33.3 | 33.3 | 33.3 | 33.3 | 33.3 |
| Total (%) | 100 | 100 | 100 | 100 | 100 |
| Ag % | 14.2 | 14.2 | 14.2 | 14.2 | 14.2 |
| F % | 2.5 | 2.5 | 2.5 | 2.5 | 2.5 |
| Ag/SCN mole ratio | NA | NA | NA | NA | NA |
| Precipitate formed upon initial addition of additional dry components | Yes | Yes | Yes | Yes | Yes |
| Precipitate dissolved after further addition of dry components | No | No | No | No | No |

TABLE 3

COMPARATIVE EXAMPLES CE-6 to CE-9.

| Components | CE-6 | CE-7 | CE-8 | CE-9 |
|---|---|---|---|---|
| AgF | 18.4 | 18.5 | 19.2 | 19.2 |
| Disodium hydrogen citrate sesquihydrate | 0.0 | 0.0 | 0.0 | 0.0 |
| Sodium carbonate | 0.0 | 0.0 | 0.0 | 0.0 |
| Potassium phosphate monobasic | 0.0 | 0.0 | 0.0 | 0.0 |
| $NH_4Cl$ | 22.1 | 0.0 | 0.0 | 26.9 |
| $NH_4SCN$ | 0.0 | 22.2 | 0.0 | 0.0 |
| $NH_4I$ | 22.8 | 22.2 | 26.9 | 0.0 |
| $Ca(SCN)_2$ tetrahydrate | 0.0 | 0.0 | 15.4 | 15.4 |
| Potassium sulfate | 0.0 | 0.0 | 0.0 | 0.0 |
| DI water | 36.8 | 37.0 | 38.5 | 38.5 |
| Total (%) | 100 | 100 | 100 | 100 |
| Ag % | 15.6 | 15.7 | 16.3 | 16.3 |
| F % | 2.8 | 2.8 | 2.9 | 2.9 |
| Ag/SCN mole ratio | NA | NA | 1.12 | 1.12 |
| Precipitate formed upon initial addition of additional dry components | Yes | Yes | Yes | Yes |
| Precipitate dissolved after further addition of dry components | No | No | No | No |

TABLE 4

EXAMPLES Ex-1 to Ex-5.

| Component | Ex-1 | Ex-2 | Ex-3 | Ex-4 | Ex-5 |
|---|---|---|---|---|---|
| AgF | 18.5 | 17.2 | 19.6 | 16.7 | 20.8 |
| $NH_4SCN$ | 0.0 | 0.0 | 35.3 | 0.0 | 31.3 |
| $Ca(SCN)_2$ tetrahydrate | 44.5 | 48.3 | 5.9 | 46.7 | 14.6 |
| DI water | 37.0 | 34.5 | 39.2 | 36.7 | 33.3 |
| Total (%) | 100 | 100 | 100 | 100 | 100 |
| Ag % | 15.7 | 14.6 | 16.7 | 14.2 | 17.7 |
| F % | 2.8 | 2.6 | 2.9 | 2.5 | 3.1 |
| Ag/SCN mole ratio | 0.37 | 0.32 | 0.30 | 0.32 | 0.30 |
| Precipitate formed upon initial addition of additional dry components | Yes | Yes | Yes | Yes | Yes |
| Precipitate dissolved after further addition of dry components | Yes | Yes | Yes | Yes | Yes |
| Formed cloudy solution after addition of all dry components and vortex mixing | Yes | Yes | Yes | Yes | Yes |
| Formed a two-layer separated solution after 1 week (bottom layer cloudy) | Yes | Yes | Yes | Yes | Yes |

TABLE 5

EXAMPLES Ex-6 to Ex-11.

| Component | Ex-6 | Ex-7 | Ex-8 | Ex-9 | Ex-10 | Ex-11 |
|---|---|---|---|---|---|---|
| AgF | 20.8 | 20.0 | 21.3 | 22.2 | 20.8 | 20.4 |
| $NH_4SCN$ | 25.0 | 20.0 | 36.2 | 37.8 | 37.5 | 36.7 |
| $Ca(SCN)_2$ tetrahydrate | 20.8 | 28.0 | 8.5 | 4.4 | 4.2 | 6.1 |
| DI water | 33.3 | 32.0 | 34.0 | 35.6 | 37.5 | 36.7 |
| Total (%) | 100 | 100 | 100 | 100 | 100 | 100 |
| Ag % | 17.7 | 17.0 | 18.1 | 18.9 | 17.7 | 17.4 |
| F % | 3.1 | 3.0 | 3.2 | 3.3 | 3.1 | 3.1 |
| Ag/SCN mole ratio | 0.32 | 0.31 | 0.30 | 0.38 | 0.36 | 0.35 |
| Precipitate formed upon initial addition of additional dry components | Yes | Yes | Yes | Yes | Yes | Yes |
| Precipitate dissolved after further addition of dry components | Yes | Yes | Yes | Yes | Yes | Yes |
| Formed cloudy solution after addition of all dry components and vortex mixing | Yes | Yes | Yes | Yes | Yes | Yes |

TABLE 5-continued

EXAMPLES Ex-6 to Ex-11.

| Component | Ex-6 | Ex-7 | Ex-8 | Ex-9 | Ex-10 | Ex-11 |
|---|---|---|---|---|---|---|
| Formed a two-layer separated solution after 1 week (bottom layer cloudy) | Yes | Yes | Yes | Yes | Yes | Yes |

TABLE 6

EXAMPLES Ex-12 to Ex-16, and COMPARATIVE EXAMPLE CE-10.

| Component | Ex-12 | Ex-13 | Ex-14 | Ex-15 | Ex-16 | CE-10 |
|---|---|---|---|---|---|---|
| AgF | 20.0 | 19.6 | 18.5 | 17.9 | 20.6 | 14.3 |
| $NH_4SCN$ | 36.0 | 35.3 | 0.0 | 0.0 | 41.2 | 28.6 |
| $Ca(SCN)_2$ tetrahydrate | 8.0 | 9.8 | 51.9 | 50.0 | 1.2 | 0.0 |
| DI water | 36.0 | 35.3 | 29.6 | 32.1 | 37.0 | 57.1 |
| Total (%) | 100 | 100 | 100 | 100 | 100 | 100 |
| Ag % | 17.0 | 16.7 | 15.7 | 15.2 | 17.5 | 12.1 |
| F % | 3.0 | 2.9 | 2.8 | 2.7 | 3.1 | 2.1 |
| Ag/SCN mole ratio | 0.34 | 0.33 | 0.38 | 0.38 | 0.35 | 0.35 |
| Precipitate formed upon initial addition of additional dry components | Yes | Yes | Yes | Yes | Yes | Yes |
| Precipitate dissolved after further addition of dry components | Yes | Yes | Yes | Yes | Yes | Yes |
| Formed cloudy solution after addition of all dry components and vortex mixing | Yes | Yes | Yes | Yes | Yes | No |
| Formed a two-layer separated solution after 1 week. (bottom layer cloudy) | Yes | Yes | Yes | Yes | Yes | No |

TABLE 7

EXAMPLES Ex-17 to Ex-18, and COMPARATIVE EXAMPLES CE-11 to CE-13. Shows Silver to Thiocyanate Mole Ratio must be <0.40:1 to Dissolve Precipitate.

| Component | CE-11 | EX17 | EX-18 | CE-12 | CE-13 |
|---|---|---|---|---|---|
| AgF | 23.8 | 21.3 | 20.0 | 22.7 | 22.2 |
| $Ca(SCN)_2$ tetrahydrate | 9.5 | 8.5 | 8.0 | 9.1 | 8.9 |
| $NH_4SCN$ | 19.0 | 27.7 | 32.0 | 22.7 | 24.4 |
| DI water | 47.6 | 42.6 | 40.0 | 45.5 | 44.4 |
| Total (%) | 100 | 100 | 100 | 100 | 100 |
| Ag % | 20.2 | 18.1 | 17.0 | 19.3 | 18.9 |
| F % | 3.6 | 3.2 | 3.0 | 3.4 | 3.3 |
| Ag/SCN mole ratio | 0.56 | 0.38 | 0.32 | 0.47 | 0.44 |
| Precipitate formed upon initial addition of additional dry components | Yes | Yes | Yes | Yes | Yes |
| Precipitate dissolved after further addition of dry components | No | Yes | Yes | No | No |
| Formed cloudy solution after addition of all dry components and vortex mixing | N/A | Yes | Yes | N/A | N/A |
| Formed a two-layer separated solution after 1 week (bottom layer cloudy) | N/A | Yes | Yes | N/A | N/A |

TABLE 8

EXAMPLES: Ex-19 to Ex-23, and COMPARATIVE EXAMPLE CE-14. Shows Total Water % must be <57%.

| Component | Ex-19 | Ex-20 | Ex-21 | Ex-22 | Ex-23 | CE-14 |
|---|---|---|---|---|---|---|
| AgF | 23.3 | 20.8 | 18.2 | 16.1 | 15.2 | 13.7 |
| $Ca(SCN)_2$ tetrahydrate | 7.0 | 6.3 | 5.5 | 4.8 | 4.5 | 4.1 |
| $NH_4SCN$ | 41.9 | 37.5 | 32.7 | 29.0 | 27.3 | 24.7 |
| DI water | 27.9 | 35.4 | 43.6 | 50.0 | 53.0 | 57.5 |
| Total (%) | 100 | 100 | 100 | 100 | 100 | 100 |
| Total water % | 30.1 | 37.4 | 45.4 | 51.5 | 54.5 | 58.8 |
| Ag % | 19.8 | 17.7 | 15.5 | 13.7 | 12.9 | 11.6 |

TABLE 8-continued

EXAMPLES: Ex-19 to Ex-23, and COMPARATIVE EXAMPLE
CE-14. Shows Total Water % must be <57%.

| Component | Ex-19 | Ex-20 | Ex-21 | Ex-22 | Ex-23 | CE-14 |
|---|---|---|---|---|---|---|
| F % | 3.5 | 3.1 | 2.7 | 2.4 | 2.3 | 2.1 |
| Ag/SCN mole ratio | 0.30 | 0.30 | 0.30 | 0.30 | 0.30 | 0.30 |
| Precipitate formed upon initial addition of additional dry components | Yes | Yes | Yes | Yes | Yes | Yes |
| Precipitate dissolved after further addition of dry components | Yes | Yes | Yes | Yes | Yes | No |
| Formed cloudy solution after addition of all dry components and vortex mixing | Yes | Yes | Yes | Yes | Yes | N/A |
| Formed a two-layer separated solution after 1 week (bottom layer cloudy) | Yes | Yes | Yes | Yes | Yes | N/A |

Example Ex-24

Silver diamine fluoride water solution (38%) from Elevate Oral Care was used as the source of silver and fluoride. An amount of 0.122 gram of silver diamine fluoride solution was mixed with 0.025 gram of $NH_4SCN$ and 0.100 gram of $Ca(SCN)_2$ tetrahydrate. Initially a precipitate was formed. The precipitate dissolved and formed a solution after mixing in the weighing boat.

Light Sensitivity of Examples

The following examples demonstrated that solutions of the inventive composition do not turn black after (1) being precipitated with the addition of a buffer solution (to mimic saliva in the oral environment), and (2) exposure to light using 3M ELIPAR DEEPCURE-S LED curing light.

Comparative Example CE-15

An amount of 58 mg of silver diamine fluoride solution (ADVANTAGE ARREST silver diamine fluoride solution (38%)) was mixed with 108 mg of 1% $KH_2PO_4$ water solution. The mixture formed a precipitate and released ammonia. The mixture was exposed to a blue LED light using 3M ELIPAR DEEPCURE-S LED curing light, with wavelength around 450 nm and output approximately 1500 $mW/cm^2$ for 20 seconds, and the mixture turned black.

Example Ex-25

An amount of 35 mg of Ex-22 solution was mixed with 90 mg of 1% $KH_2PO_4$ water solution. The mixture formed a precipitate. The mixture was exposed to a blue LED light using 3M ELIPAR DEEPCURE-S LED curing light, with wavelength around 450 nm and output approximately 1500 $mW/cm^2$ for 20 seconds. The mixture did NOT turn black.

Example Ex-26

An amount of 40 mg of Ex-24 solution was mixed with 104 mg of 1% $KH_2PO_4$ water solution. The mixture formed a precipitate. The mixture was exposed to a blue LED light using 3M ELIPAR DEEPCURE-S LED curing light, with wavelength around 450 nm and output approximately 1500 $mW/cm^2$ for 20 seconds. The mixture did NOT turn black.

Tooth Dentin Surface Treatment and Characterization

Bovine teeth were polished with 120 grit sandpaper to expose the dentin, then 320 grit sand paper was used to polish the dentin surface. The dentin was etched to clean the dentin surface for 10 seconds using SCOTCHBOND UNIVERSAL ETCHANT (commercially available from 3M Company, St. Paul, Minn.). The etched bovine teeth were rinsed with water to clear the surface, then the teeth were blow-dried with pressurized air. The prepared dentin surfaces (teeth) were painted with different Example and Comparative Example solutions, allowed to sit for a minute, rinsed with water, and then air dried before evaluation using a table-top scanning electron microscope. The prepared dentin control and the prepared dentin treated with Example and Comparative Example solutions were examined by a Hitachi TM3000 SEM to observe the structure and characteristics of the coatings deposited on the dentin surface.

Comparative Example CE-16

Figure 1:
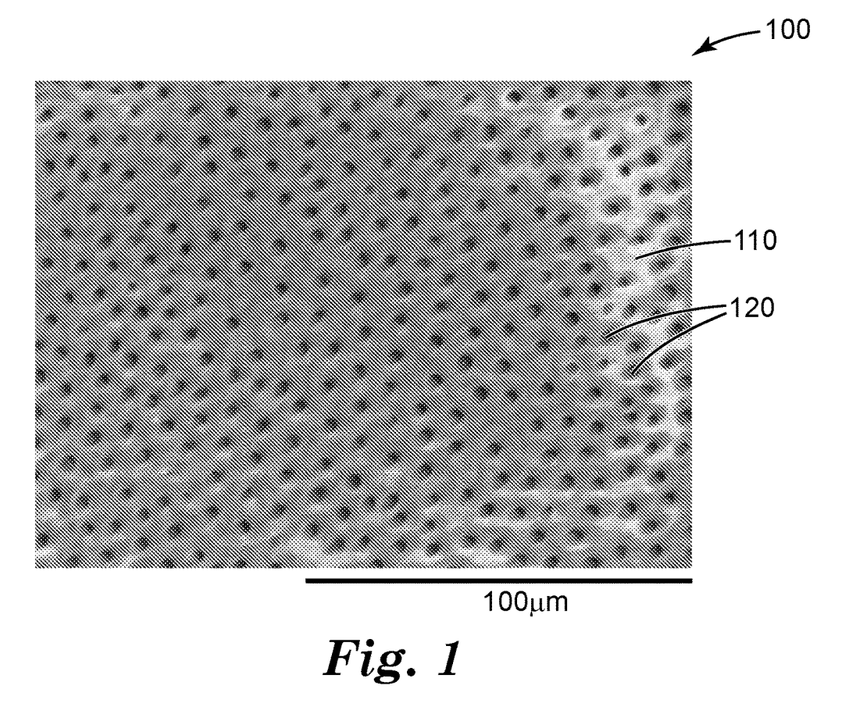
FIG. 1 is a Scanning Electron Micrograph (SEM) of the material of Comparative Example CE-16, which is a control dentin surface that was not treated.

Comparative Example CE-16 was the control prepared dentin surface that was not treated with Example or Comparative Example solution and was evaluated by SEM. The SEM of CE-16 is shown in FIG. 1. The acid etched, washed, and dried tooth surface 100 shows the cleaned dentin surface 110 and the many dentin tubule openings 120.

Comparative Example CE-17

Comparative Example CE-17 was the prepared dentin surface that was treated with Comparative Example CE-10 solution, which does not contain $Ca(SCN)_2$ tetrahydrate, and was evaluated by SEM. The SEM of CE-17 is shown in FIG. 2. The acid etched, washed, and dried tooth surface 200 shows the cleaned dentin surface 210 covered with dried CE-1 solution. The SEM shows the dentin tubule openings 220 and the "snow flake-like" silver crystals 230, dried on the dentin surface.

Example Ex-27

Example Ex-27 was the prepared dentin surface that was treated with Example Ex-7 solution, which contains $Ca(SCN)_2$ tetrahydrate, and was evaluated by SEM. The SEM of Ex-27 is shown in FIG. 3. The acid etched, washed, and dried tooth surface 300 shows the cleaned dentin surface 310 covered with dried Ex-7 solution. The SEM shows the dentin tubule openings 320, the "snow flake-like" silver crystals 330 and the separate calcium fluoride layer 340, dried on the dentin surface.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An aqueous oral care solution comprising:
   silver cations;
   thiocyanate anions provided by a thiocyanate source comprising $Ca(SCN)_2$; fluoride anions; and
   water in an amount of up to 57 wt-%, based on the total weight of the solution;
   wherein the molar ratio of silver to thiocyanate ions is up to 0.40:1.

2. The oral care solution of claim 1 comprising:
   12.5-20.2 wt-% silver cations; and
   1.0-6.0 wt-% fluoride anions;
   wherein the weight percentages are based on the total weight of the solution;
   wherein the molar ratio of silver to thiocyanate ions is at least 0.10:1 and up to 0.40:1; and
   wherein the oral care solution forms a precipitate upon contact with additional water or saliva.

3. The oral care solution of claim 2 comprising:
   12.5-20.2 wt-% silver cations; and
   2.2-3.5 wt-% fluoride anions.

4. The oral care solution of claim 1, comprising 1-55 wt-% $Ca(SCN)_2$.

5. The oral care solution of claim 1, comprising a source of silver cations selected from silver fluoride, silver chloride, silver nitrate, silver diamine fluoride, and combinations thereof.

6. The oral care solution of claim 1, comprising a source of fluoride anions selected from silver fluoride, silver diamine fluoride, sodium fluoride, ammonium fluoride, potassium fluoride, amine fluoride, and combinations thereof.

7. The oral care solution of claim 1, comprising a secondary source of thiocyanate anions selected from ammonium thiocyanate, sodium thiocyanate, potassium thiocyanate, guanidinium thiocyanate, and combinations thereof.

8. The oral care solution of claim 1, further comprising a thickener.

9. The oral care solution of claim 1, which has a pH of 5.5 to 9.

10. The oral care solution of claim 1, comprising less than 5 wt-% organic solvent.

11. The oral care solution of claim 1, comprising at least 20 wt-% water, based on the total weight of the solution.

12. The oral care solution of any of claim 1, further comprising one or more active agents.

13. The oral care solution of claim 1, further comprising calcium cations.

14. The oral care solution of claim 1, further comprising a surfactant.

15. The oral care solution of claim 1, which does not stain teeth.

16. A method of providing fluoride to a patient's tooth surface, the method comprising applying the aqueous oral care solution of claim 1, to the patient's tooth surface.

17. A method of reducing the incidence of dental caries in a patient in need thereof, the method comprising applying an aqueous oral care solution of claim 1, to the patient's tooth surface.

18. A method of reducing dentin sensitivity and/or root sensitivity in a patient in need thereof, the method comprising applying an aqueous oral care solution of claim 1, to the patient's tooth surface.

19. A kit comprising an aqueous oral care solution of claim 1, and an applicator.

* * * * *